(12) United States Patent
Schleicher

(10) Patent No.: US 6,386,503 B1
(45) Date of Patent: May 14, 2002

(54) MOLD FOR EMBEDDING CASTS IN AN EMBEDDING COMPOUND FOR PRODUCING MOLDS FOR DENTAL WORKPIECES

(75) Inventor: Wolfgang Schleicher, Riedenburg (DE)

(73) Assignee: Dental Forschung Schleicher GmbH, Riedenburg (DE)

( * ) Notice: Subject to any disclaimer, the term of this patent is extended or adjusted under 35 U.S.C. 154(b) by 0 days.

(21) Appl. No.: 09/477,450

(22) Filed: Jan. 4, 2000

(30) Foreign Application Priority Data

| Jan. 8, 1999 | (DE) | 299 00 179 U |
| Jun. 16, 1999 | (DE) | 299 10 525 U |
| Nov. 20, 1999 | (DE) | 199 55 866 |

(51) Int. Cl.[7] .............................................. B29C 39/26
(52) U.S. Cl. ........................ 249/54; 249/157; 249/173; 425/173; 425/180; 264/17; 164/DIG. 4
(58) Field of Search .................... 249/54, 173, 160, 249/164, 157; 164/DIG. 4; 264/17; 425/175, 180, 173

(56) References Cited

U.S. PATENT DOCUMENTS

| 1,050,816 A | * | 1/1913 | Deslauriers | 249/157 |
| 3,527,439 A | * | 9/1970 | Lawmaster | 249/164 |
| 3,610,317 A | * | 10/1971 | Benfield | 164/238 |
| 3,956,437 A | * | 5/1976 | Ellis | 249/157 |
| 4,777,996 A | * | 10/1988 | Finelt | 164/237 |
| 5,183,095 A | * | 2/1993 | Sullivan | 164/34 |
| 5,275,545 A | * | 1/1994 | Ohyamagi et al. | 425/173 |
| 5,360,052 A | * | 11/1994 | Tomic et al. | 164/412 |
| 5,406,999 A | * | 4/1995 | Berger et al. | 164/376 |
| 5,688,533 A | * | 11/1997 | Berger | 249/54 |

* cited by examiner

Primary Examiner—Nam Nguyen
Assistant Examiner—Thu Khanh T. Nguyen
(74) Attorney, Agent, or Firm—Hoffman, Wasson & Gitler, PC

(57) ABSTRACT

A mold for embedding casts in an embedding compound for producing molds for dental workpieces, such as crowns and bridges, which has a mold cavity which can be filled with the embedding compound, which holds at least one cast and which is closed by a cylindrical peripheral wall and by a bottom part. The peripheral wall is formed by a blank of a transparent or translucent flat elastic material.

15 Claims, 5 Drawing Sheets

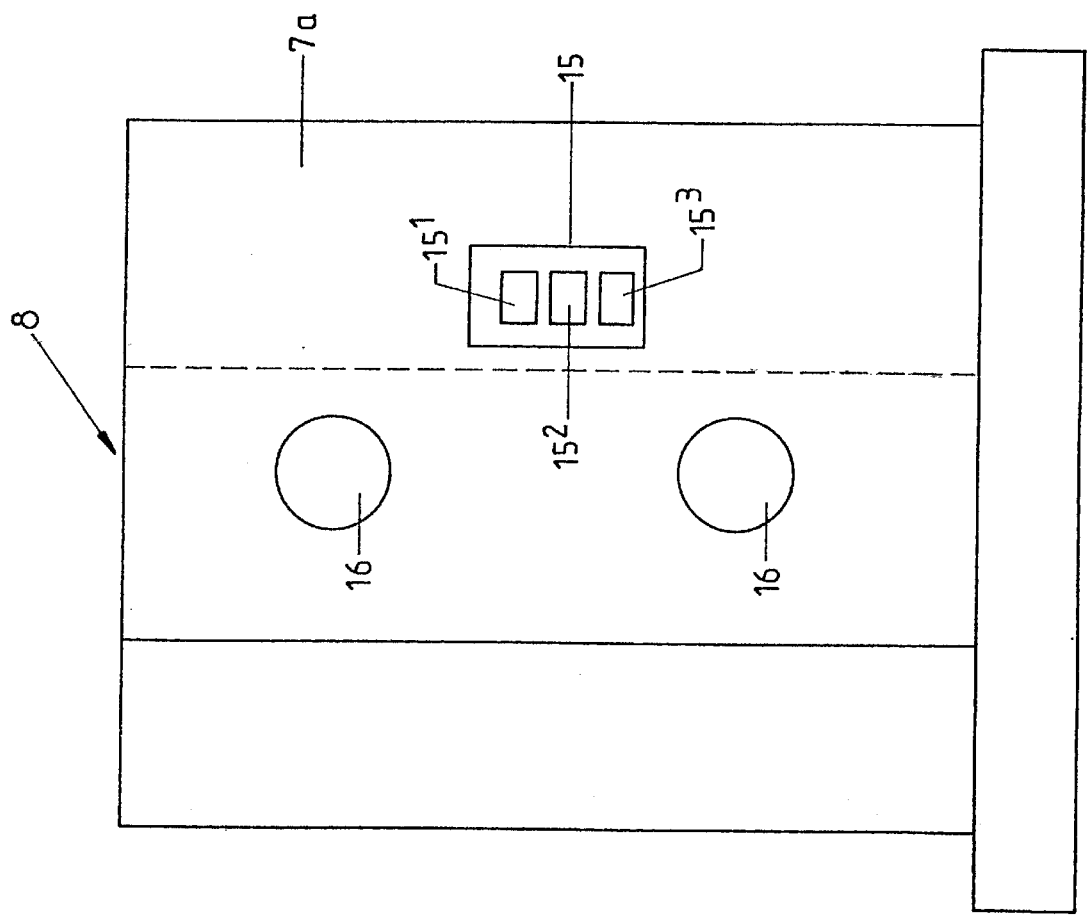

MOLD FOR EMBEDDING CASTS IN AN EMBEDDING COMPOUND FOR PRODUCING MOLDS FOR DENTAL WORKPIECES

BACKGROUND OF THE INVENTION

The invention relates to a mold for embedding casts in an embedding compound for producing molds for dental workpieces, such as crowns and bridges.

Dental workpieces, for the purposes of the invention, are defined as crowns and bridges. An embedding mold for producing a casting mold for these types of dental workpieces is known (DE 85 19 112).

The object of the invention is to provide an embedding mold which compared to the known embedding mold provides improvement and simplification of handling while maintaining precision with respect to the resulting molds.

SUMMARY OF THE INVENTION

In the mold as described by the invention, a wall of an open blank of film is produced from transparent, preferably crystal-clear or essentially crystal-clear plastic. This film is rolled together into a wall which surrounds the mold cavity with overlapping of the film ends. The film ends are held together and the film is supported by the outer sleeve.

After completing the mold, i.e. after curing of the embedding compound, preferably before final curing, the wall can be removed especially easily and quickly by simple lifting of the sleeve and by unwinding the blank which forms the wall.

BRIEF DESCRIPTION OF THE FIGURES

The invention is detailed below using the following figures:

FIG. 6 shows the embodiment of FIG. 5 in a simplified side view.

DETAILED DESCRIPTION OF THE INVENTION

Figure 1:
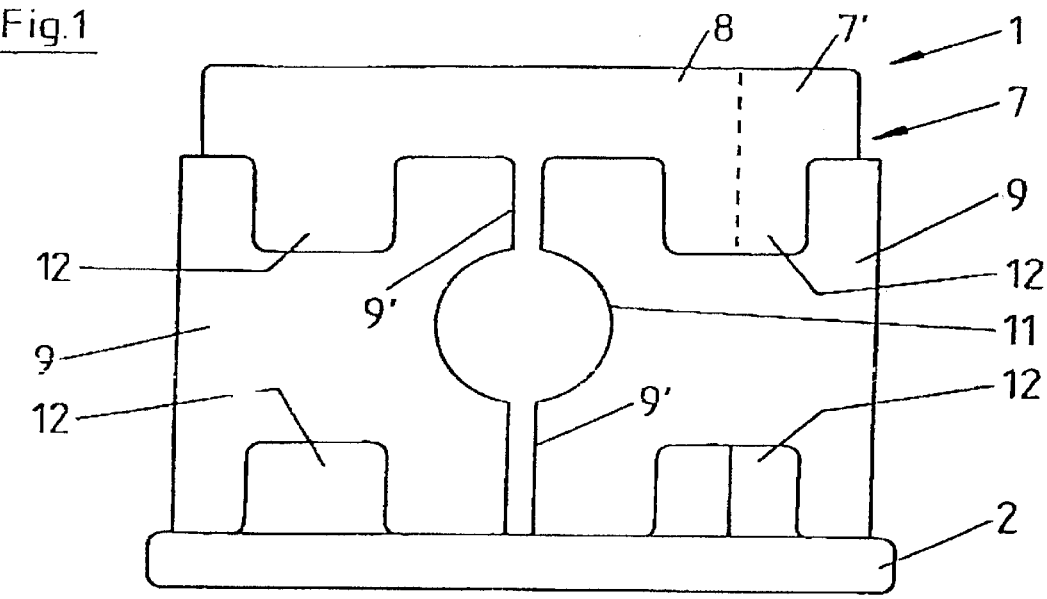
FIG. 1 shows in a simplified representation and in a side view an embedding mold as claimed in the invention.

The embedding mold 1 shown in FIGS. 1–4 contain a bottom part 2 which is produced in the shape of a round disk from hard rubber or another elastic material. In the middle area, the bottom part 2 has a projection 3 which is shaped like a truncated cone, which is rounded on the top, and which is made concentric to one axis of symmetry, or the center axis S of the bottom part 2. On the side which has the projection 3, the bottom part 2 has a ring-shaped gradation 4 which symmetrically surrounds the axis of symmetry, radially offset to the outside, relative to the projection 3. The gradation forms a circular cylindrical surface 4' which concentrically surrounds the axis of symmetry S and a subsequent annular surface 4" which lies in one plane perpendicular to the axis of symmetry S, underneath the top of the bottom part 2 which has the projection 3. On the gradation 4, the bottom part 2 is produced in one piece with a peripheral sealing lip 5 which concentrically surrounds the axis of symmetry S and which in the representation chosen for FIG. 3, i.e. the bottom part 2 removed from the other elements of the embedding mold, protects over the surface 4'. The sealing lip 5, in this embodiment, is repeatedly interrupted or indented at 6.

Figure 4:
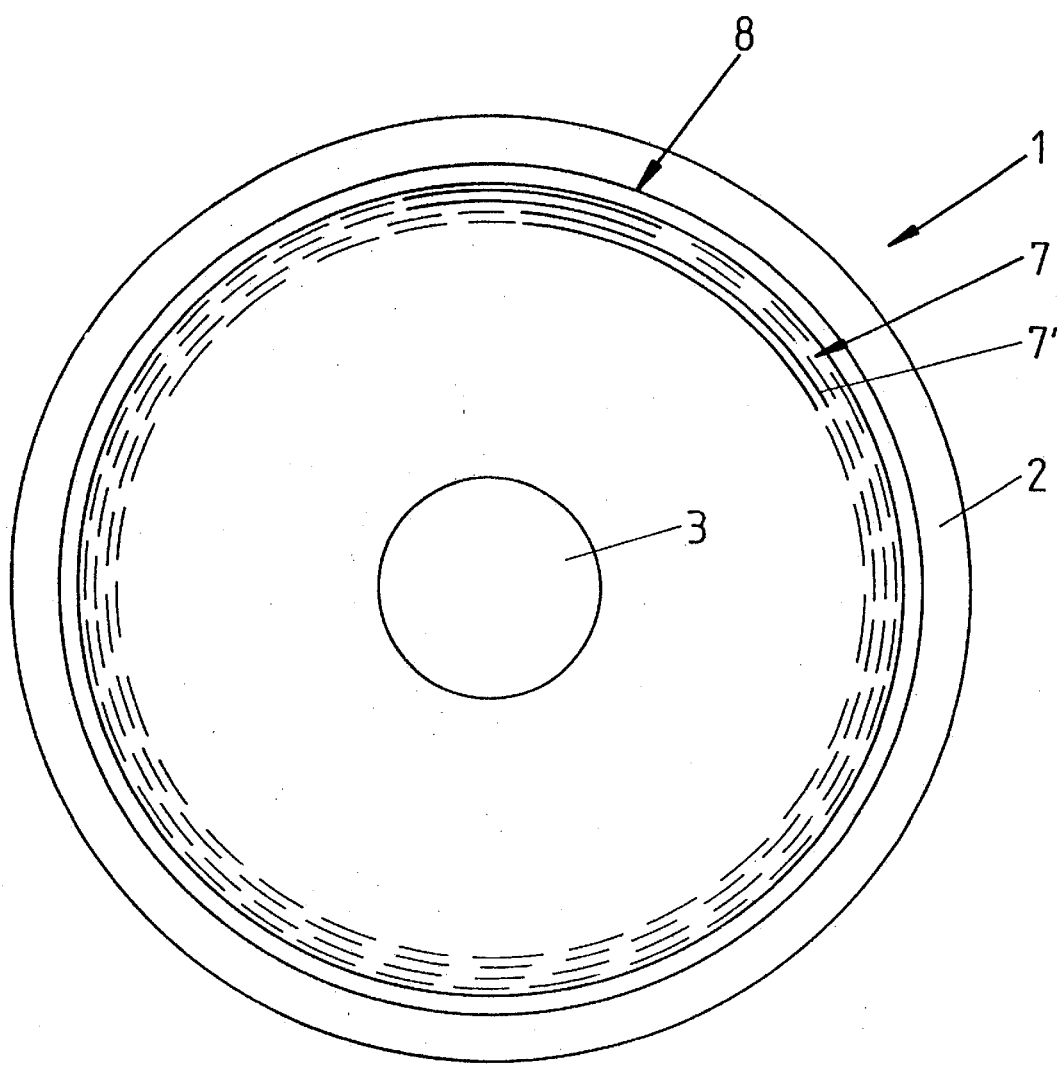
FIG. 4 shows an overhead view of the bottom part of the embedding mold of FIGS. 1 and 2.

The embedding mold 1 has a circular cylindrical wall 7 which is attached to the bottom part 2 and concentrically surrounds the axis of symmetry S and which is produced from an open blank 7' of transparent or translucent film, from a plastic material which ensures a certain strength or stiffness for the wall 7. As is indicated in FIG. 4, the blank 7' is rolled together into the wall 7 such that the two ends of the blank overlap at 8 without the ends of the blank being interconnected, so that an increase of the diameter of the interior space of the embedding mold 1 is possible without the wall 7 counteracting one such increase in diameter with a significant opposing force.

The wall 7 has its lower edge resting on the surface 4" and in the area of the lower edge, has its inner surface lying against the surface 4' and also against the sealing lip 5 so that a tight seal is achieved. By means of the notches 6 the sealing lip 5 can follow a change of the inside diameter of the embedding mold almost without force. An outer sleeve is labelled 9; it surrounds the wall 7 at least on one part of the height of the embedding mold 1 and is produced from a harder plastic material. The sleeve 9 is continuously slotted, at a position so that the sleeve 9 on the two ends 9', which are formed by the slot 10, can be opened or bent away from one another elastically such that the sleeve 9 can be mounted and dismounted on or from the wall 7. The sleeve 9 in its mounted state holds the wall 7 together.

To simplify handing of the sleeve 9, it is provided on its ends 9' with one recess 11 which forms a gripping surface. Furthermore, the sleeve 9 is provided with various recesses or windows 12 through which, with the embedding mold 1 completely assembled, the interior of the embedding mold also remains visible from the side, through the film which forms the wall 7.

In the conventional manner, the cast 13 of a crown or bridge is attached to the conical projection 3 via a bridge-like element 14 which is produced from the casting compound (wax) and later forms the casting channel when casting the crown or bridge.

The embedding mold is used, such that after assembling the mold and placing the respective cast 13 in the interior of the embedding mold, the embedding compound is placed in the embedding mold from the open top, and this insertion can be observed not only from the top, but also laterally through the window-shaped openings 11 and 12. In particular, it can be observed or ensured that the embedding compound flows optimally into the cavity of the cast 13 without air inclusions remaining here.

Figure 2:
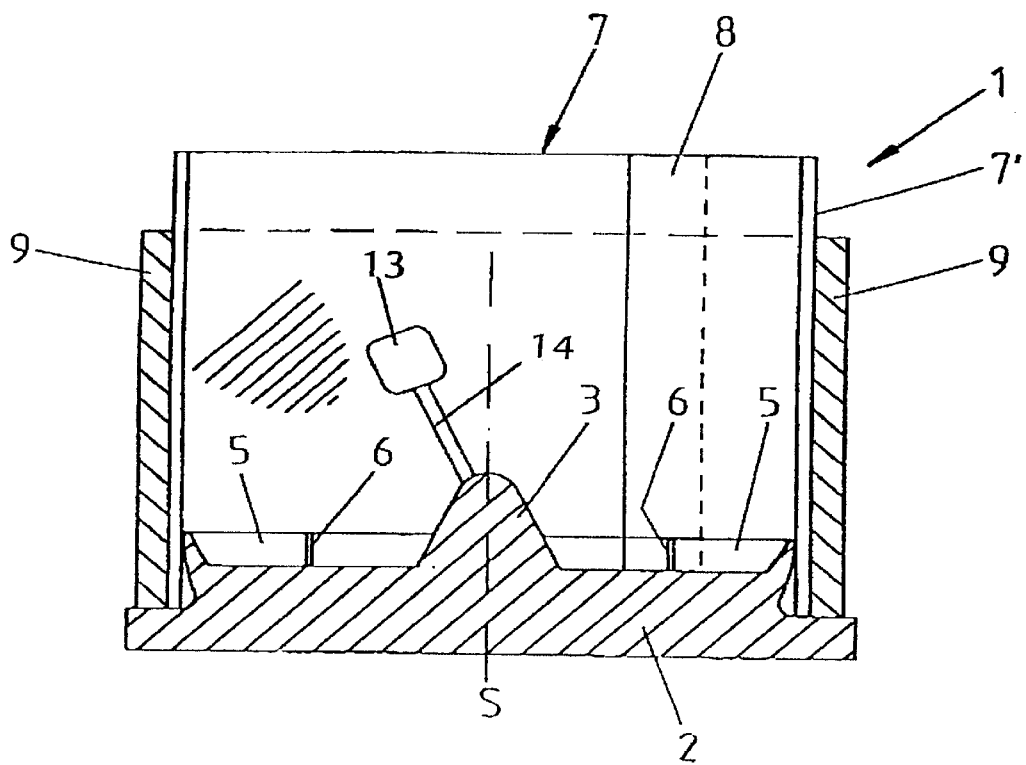
FIG. 2 shows the mold from FIG. 1 in a lengthwise section.
Figure 3:
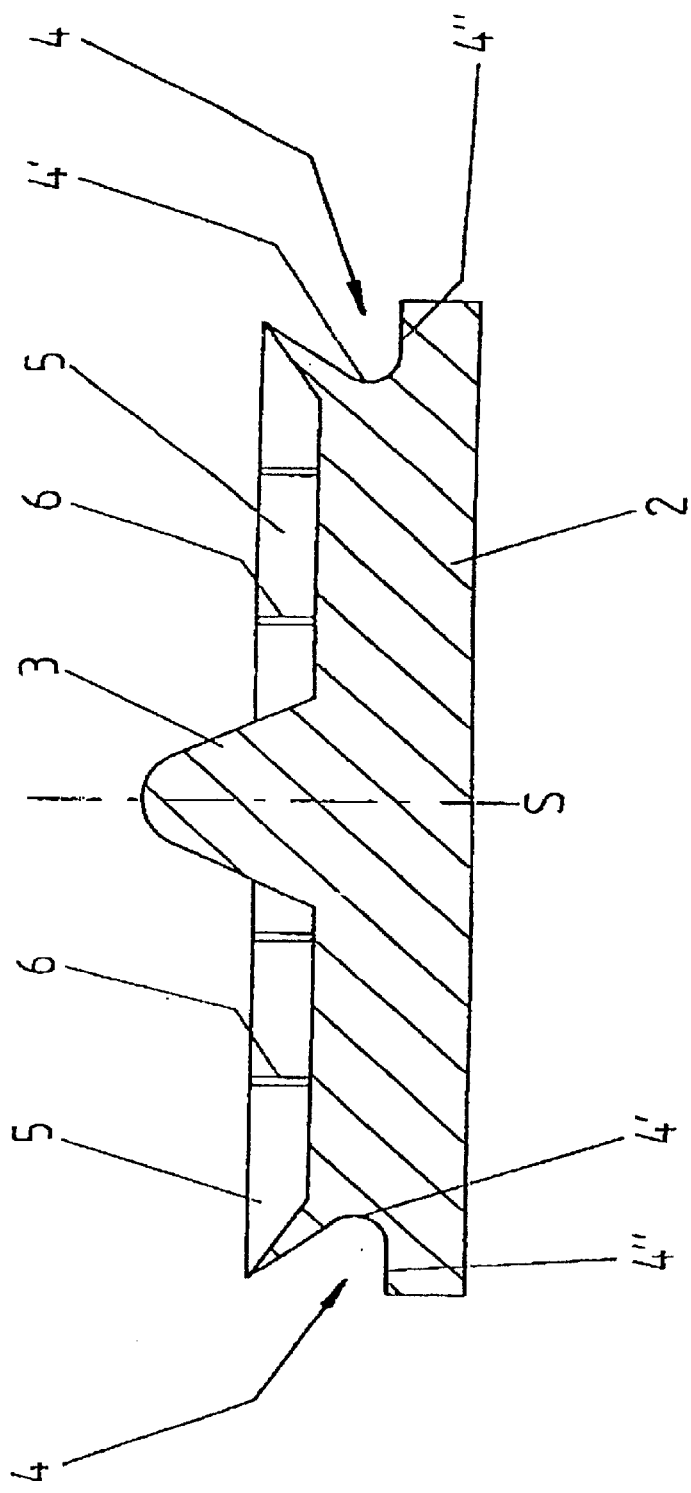
FIG. 3 shows the bottom part in an individual representation.

As FIGS. 1 and 2 show, the wall 7 projects over the top edge of the sleeve 9. This makes it easy to check the fill level of the embedding mold with the embedding compound, especially to prevent too much embedding mass from being placed in the embedding mold 1 and thus flowing over the top edge; this would make it difficult to open the embedding mold after curing of the embedding masses.

As is recognized, the embedding compounds used are made such that during curing, but especially when a certain solid state has been achieved during curing, the compounds expand in order to compensate for the shrinkage of the metal-cast crown or bridge which is caused by cooling, by increasing the size of the mold cavity formed by the respective cast 13 in the embedding compound. Even small forces or constraints can disrupt this expansion process, for example, such that when the expansion process is limited or restricted by the wall 7, the expansion process is intensified in the direction of the axis of symmetry S, by which the crown or bridge produced then has overly large dimensions in this axial direction, while in the axial directions which run perpendicularly thereto the dimensions are below the desired value.

It has been found that the above described formation of the peripheral wall and also the division of the sealing lip 5 keep the forces or constraints opposing the expansion of the embedding compound so small that radially to the axis of symmetry S the desired dimensions are maintained with high precision for the mold cavity formed by the cast 13.

Important components of the embedding mold 1 are the cylindrical peripheral wall 7 which is produced by the blank 7' of transparent plastic, the sleeve 9 which supports this peripheral wall, and the bottom part 2 with the self-supporting sealing lip which has been repeatedly notched at 6.

Figure 5:
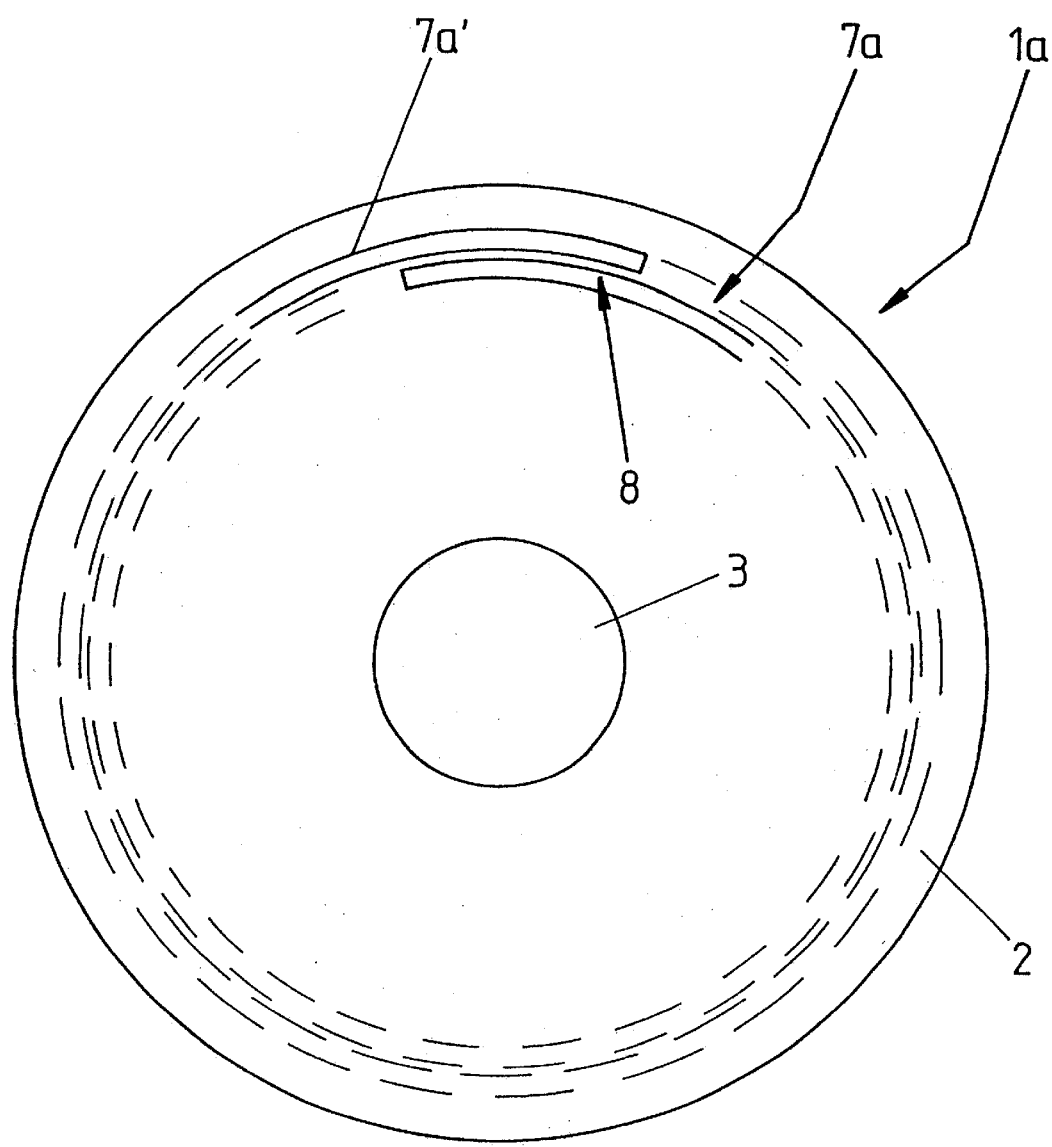
FIG. 5 shows in a representation similar to FIG. 4 another embodiment of the mold as claimed in the invention.

FIGS. 5 and 6 show another possible embodiment in which the wall 7a which surrounds the mold cavity is produced from transparent material. The material is chosen such that the wall 7a already has the necessary strength. The wall 7a is in turn made such that the pertinent blank 7a' overlaps itself so that when the embedding compound expands, the inside diameter of the mold internal cavity can be increased without the wall 7a becoming loose due to the divergence of the blank 7a'. Due to the self-supporting and repeatedly indented sealing lip 5 it also yields in this embodiment, when the embedding compound expands, so that unwanted deformations in the mold which has been produced in the dental workpiece are effectively prevented.

In FIG. 6, a display is labelled 15; and is provided on the blank 7a and responds to the temperature of the embedding compound during setting. This display 15 is formed, for example, by a liquid crystal temperature display which in the embodiments shown has three fields $15^1$, $15^2$, and $15^3$ which each are activated at different temperatures and then appear in different colors. For example, field $15^1$ is red at low temperature, meaning that the embedding mold must still be kept closed, field $15^2$ is yellow at a somewhat higher temperature, meaning that the embedding mold should be opened as soon as possible, and field $15^3$ is green, meaning that at this point the embedding mold should be opened immediately.

The display 15 prevents uncontrolled expansion of the embedding compound by too early opening of the embedding mold and thus by too early release; this expansion leads to cracks in the embedding compound or in the mold which has been produced. In FIG. 6, two velcro closures are labelled 16; they are used to interconnect the overlapping ends in the area of the overlap 8 without the desired elasticity of the wall 7a being lost.

The invention was described above using various embodiments. It goes without saying that changes and modifications are possible without in this way departing from the inventive idea underlying the invention.

| Reference number list | |
| --- | --- |
| 1, 1a | embedding mold |
| 2 | bottom part |
| 3 | projection |
| 4 | gradation |

| -continued | |
| --- | --- |
| Reference number list | |
| 4', 4" | surface |
| 5 | sealing lip |
| 6 | indent |
| 7, 7a | wall |
| 7', 7a' | blank of transparent material |
| 8 | overlap |
| 9 | sleeve |
| 9' | end |
| 10 | slot |
| 11, 12 | recess |
| 13 | cast |
| 14 | bridge-like section |
| 15 | temperature display |
| $15^1$, $15^2$, $15^3$ | field |
| 16 | velcro closure |

What is claimed is:

1. A mold assembly for embedding casts in an embedding compound for producing molds for casting dental workpieces, crowns and bridges,
    said mold assembly comprising a cavity for receiving said casts, said cavity being closed by a cylindrical peripheral wall and a bottom part,
    wherein the cylindrical peripheral wall is formed by a blank of a transparent or a translucent elastic material, said blank having two ends that overlap to form a closed cylindrical peripheral wall without the ends being connected to one another,
    the bottom part having a sealing lip which adjoins an inner surface of the cylindrical peripheral wall to seal a passage between the bottom part and the cylindrical peripheral wall.

2. The mold assembly as claimed in claim 1, further comprising:
    a slotted sleeve surrounding the peripheral wall on its outside for supporting said blank which forms said peripheral wall.

3. The mold assembly as claimed in claim 2, wherein said sleeve is made as a slotted circular cylinder.

4. The mold assembly as claimed in claim 2, wherein the sleeve is a transparent or a translucent material.

5. The mold assembly as claimed in claim 2, wherein the sleeve has openings or recesses which form viewing windows.

6. The mold assembly as claimed in claim 2, wherein the sleeve consists of an elastic plastic.

7. The mold assembly as claimed in claim 2, wherein the sleeve, in an area of an end of the sleeve, has a slot which has a recess which forms a grip surface.

8. The mold assembly as claimed in claim 1, wherein the sealing lip stands away from the bottom part.

9. The mold assembly as claimed in claim 1, wherein the sealing lip is repeatedly notched.

10. The mold assembly as claimed in claim 1, wherein the blank which forms the cylindrical peripheral wall has overlapping ends connected by a hook and loop type closure.

11. A mold assembly for embedding casts in an embedding compound for producing molds for casting dental workpieces, crowns and bridges,
    said mold assembly comprising a cavity for receiving said casts, said cavity being closed by a cylindrical peripheral wall and a bottom part,
    wherein the cylindrical peripheral wall is formed by a blank of a transparent or a translucent elastic material, said blank having two ends that overlap to form a closed cylindrical peripheral wall without the ends being connected to one another, the bottom part having a sealing lip which adjoins an inner surface of the cylindrical peripheral wall to seal a passage between the bottom part and the cylindrical peripheral wall, a slotted sleeve surrounding the peripheral wall on its outside for supporting said blank which forms said peripheral wall, and a display on the cylindrical peripheral wall which response to a temperature of the embedding compound during curing.

12. mold assembly for embedding casts in an embedding compound for producing molds for casting dental workpieces, crowns and bridges, said mold assembly comprising a cavity for receiving said casts, said cavity being closed by a cylindrical peripheral wall and a bottom part, wherein the cylindrical peripheral wall is formed by a blank of a transparent or a translucent elastic material, said blank having two ends that overlap to form a closed cylindrical peripheral wall without the ends being connected to one another, the bottom part having a sealing lip which adjoins an inner surface of the cylindrical peripheral wall to seal a passage between the bottom part and the cylindrical peripheral wall, and a display on the cylindrical peripheral wall which response to a temperature of the embedding compound during curing.

13. The mold assembly as claimed in claim 12, wherein the sealing lip stands away from the bottom.

14. The mold assembly as claimed in claim 12, wherein the sealing lip is repeatedly notched.

15. The mold assembly as claimed in claim 12, wherein the blank which forms the cylindrical peripheral wall has overlapping ends connected by a hook and loop type closure.

* * * * *